United States Patent [19]

Drdlik

[11] 4,071,272

[45] Jan. 31, 1978

[54] CONTACT LENS APPLICATOR

[76] Inventor: Frank J. Drdlik, 6334 Bryn Mawr, Hollywood, Calif. 90028

[21] Appl. No.: 726,937

[22] Filed: Sept. 27, 1976

[51] Int. Cl.² .............................................. A61F 9/00
[52] U.S. Cl. ................................ 294/1 CA; 294/64 R
[58] Field of Search ............... 294/1 CA, 64 R, 64 A, 294/64 B; 128/303; 351/160

[56] References Cited

U.S. PATENT DOCUMENTS

| 1,667,552 | 4/1928 | Igou | 294/64 R |
| 2,384,334 | 9/1945 | Olson | 294/64 R |
| 3,879,076 | 4/1975 | Barnett | 294/64 R |

Primary Examiner—James B. Marbert
Attorney, Agent, or Firm—Roger A. Marrs

[57] ABSTRACT

An applicator is disclosed herein for inserting and for removing a contact lens which includes a two piece construction of molded parts. One part is a pliable bulb element adapted to the snap-lock into engagement with a selected end of an elongated and flexible shank having an open-ended passageway extending therethrough and terminating in a lens seat defined by a compound concave curvature. The bulb includes internal and integrally formed ribs which strengthen the bulb wall so that the bulb may be readily depressed to expel air through the passageway of the shank so as to create a suction for holding the lens in the lens seat.

7 Claims, 2 Drawing Figures

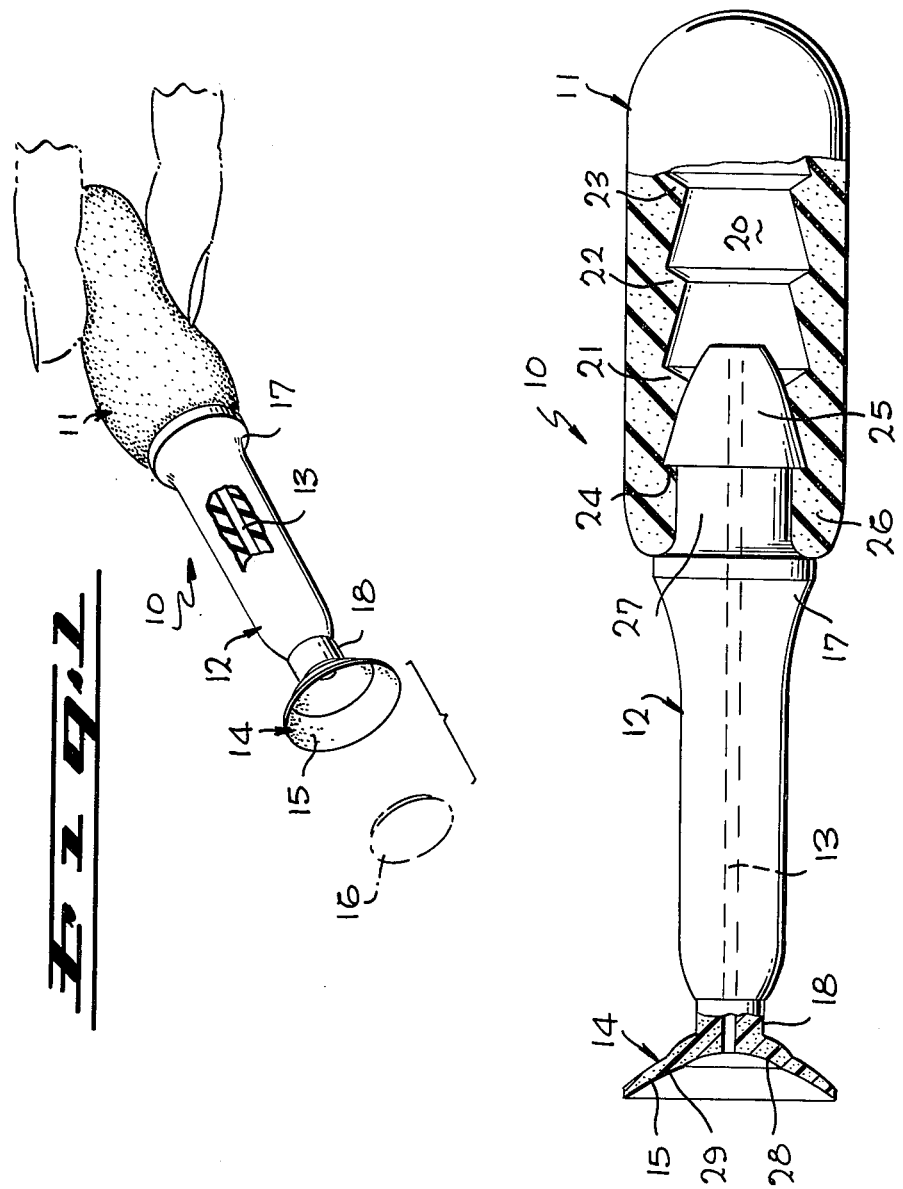

CONTACT LENS APPLICATOR

BACKGROUND OF THE INVENTION

1. Field of the Invention

The present invention relates to apparatus for inserting and for removing a contact lens and in particular, to a novel contact lens applicator which enables accurate and rapid positioning of the lens with respect to the eye during lens insertion and removal procedures.

2. Brief Description of the Prior Art

Persons in need of vision correction are turning in increasig numbers to the use of contact lenses as an alternative to the conventional frame-type eyeglasses because of the inconvenience, the cosmetic appearance, and frequently the relative safety of contact lenses. In order instances, eye correction can only be achieved through the use of contact lenses. Because of the small size of each contact lens, the users of such lenses frequently encounter difficulty in applying and removing the lenses to and from the eyes. Proper insertion of the lens requires that the lens be accurately guided to contact the eye for seating at the proper position on the eye. During a removal procedure, the device must be centered on the lens and withdrawn for separating the lens from the eye. In either instance, it is required that the applicator or device adaquately hold and subsequently release the contact lens.

Devices which attempt to accomplish the task of applying or inserting contact lenses are known in the prior art. Such devices, however, generally fail to provide a positive and accurate indication to the user that the contact lens has been accurately positioned with respect to the eye. Furthermore, some prior art contact lens applying devices require manipulation of a separate lever or movable element to elevate the contact lens into actual contact with the eye. In other instances, such as disclosed in U.S. Pat. Nos. 2,384,334; 2,379,629 and 2,919,696, a variety of vacuum and plunger type devices are set forth. These devices have no means for equalizing pressure or for reinforcing the bulb or shank of the device. Also, the devices are composed of several component pars and some of which are disposed in moving relationship to others which adds to the complexity not only in manufacture but in use of the device. It is to be borne in mind that the contact lenses are very small and that procedures involving the application or removal of the lenses to and from the eye are performed in a restrictive and sensative area of the body. Therefore, use of two hands is greatly restricted and the use of one hand whee movable parts are involved is extremely tedious.

Therefore, a long standing need is present to provide a simple and reinforced applicator for contact lenses which is capable of inserting as well as removing contact lenses from the eye. Single hand use and reinforcement of the device construction is also needed.

SUMMARY OF THE INVENTION

Accordingly, the above problems and difficulties are obviated by the present invention which provides a novel contact lens applicator and removal device which comprises a pair of molded parts or components. In one form of the invention, the device or applicator comprises a deformable or pliable bulb having an interior cavity defined by interior integral walls formed in the structure of the bulb and including a formed shoulder adapted to be snap-locked over a mating shoulder or member formed on one end of an elogated shank. The opposite end of the shank includes a compound concave curvature for seating the contact lens during use. An elongated passageway communicating the interior of the bulb with the lens seat is provided in the shank so that air may be evacuated from the interior of the bulb whereby a suitable vacuum is created for holding the lens in the lens seat on the compound concave curvature. Upon the release of the vacuum or the breaking thereof, the contact lens separates from its seat.

Therefore, it is among the primary objects of the present invention to provide a novel contact lens inserting apparatus which enables the user to accurately manipulate the contact lens during insertion or removal procedures with respect to the users eye.

Another object of the present invention is to provide a novel contact lens applicator which will provide a stronger suction grip on the lens than can be achieved by conventional devices and which will retain the suction during the manipulation of the applicator.

Still a further object of the present invention is to provide a novel contact lens applicator which is composed of molded components which are snap-locked together forming a reinforced suction device whereby the contact lens may be applied or removed from the eye of the user.

A further object of the present invention is to provide a novel pneumatic device for manipulating contact lenses which may be operated by the fingers of one hand of the user and which is economical to manufacture at a relatively inexpensive price.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood by reference to the following description, taken in connection with the accompanying drawings in which:

FIG. 1 is a front perspective view of the novel lens applicator of the present invention illustrating the applicator in use for manipulating a contact lens with respect to the eye of the user;

FIG. 2 is an enlarged longitudinal cross sectional view of the novel contact lens applicator shown in FIG. 1.

DESCRIPTION OF THE PREFERRED EMBODIMENT

Referring to FIG. 1, the novel contact lens applicator of the present invention is shown in the general direction of arrow 10 which includes a pliable or flexible bulb-like element 11 which is of a rather thin wall construction and made, preferably, of resilient material such as soft rubber or the like. The bulb element 11 is hollow and is intended to be releasably depressed by the fingers of the user as shown. The bulb element 11 is releasably carried on one end of an extension or shank 12 which is of a resilient or yieldable material similiar to the material of the bulb element 11. Preferably, the bulb element 11 and the extension or shank 12 are molded parts which are engaged together by a snap-lock fastening means. It can be seen that the extension or shank 12 is provided with an internal passageway 12 which opens at its opposite ends with the interior of the bulb element 11 and a contact lens holding element 14 respectively.

The contact element 14 includes a compound concave curvature generally illustrated by numeral 15 which forms a seat for carrying the contact lens. The lens is indicated by numeral 16 and is illustrated in the exploded view for clarification.

The extension or shank 12 is outwardly flared at numeral 17 to provide a shoulder against which the bulb element 11 may be stopped. It is to be particularly noted that the shank 12 is provided with a reduced portion or neck 18 which joins the cup or seat element 14 with the main body of the shank 12. By this means, as well as the pliable material being employed, a flexible and non-rigid device is produced. Therefore, when the applicator is touching the eye for either insertion or removal of the contact lens 16, the shank 12 will flex and bend in the event too much pressure is inadvertantly applied by the user. This is a decided advantage over rigid devices.

Referring now to FIG. 2 in detail, it can be seen that bulb element 11 is formed with a hollow interior identified by numeral 20 which is formed by defining a plurality of internal ribs such as identified by numerals 21, 22 and 23. A shoulder 24 is provided which cooperates with rib or bead at 21 for releasably securing a knob 25 carried on the end of shank or extension 12. The knob 25 is forcibly urged through an opening in the bulb element 11 towards the cavity 20 and the knob 25 seats between the stop 24 and the rib or bead 21. A collar portion of reduced diameter identified by numeral 26 forcibly engages with the outer surface of a reduced portion 27 formed in the shank immediately behind the head 25. The flange 17 of the extension or shank 12 engages with the annular end of the bulb element 11 so as to seal the opening leading into the cavity 20. The contact lens engaging portion 14 includes a concave surface 28 which is coaxially disposed with respect to an outer concave surface 29. The concave surfaces define the compound concave surface forming the lens seat so that the lens covers the opening leading to passageway 13.

The passageway 13 is employed for establishing a path for expelling air in the bulb-like element 11 when pressure is applied externally to the bulb as shown in FIG. 1. When pressure is applied to the contact lens portion 14 which constitutes a suction cup, a thin contact lens 16 may be readily picked up and held within the concave surfaces 28 and 29. In order to release the contact lens, it is only necessary to depress the bulb-like element 11 a little further than it had been depressed when picking up the contact lens. This will cause additional air to be expelled and drop the thin sheet like contact lens 16 in any particular allocation designed for it.

It is to be noted that the device is completely flexible so that the cup-like portion 14, extension or shank 12 and bulb-element 11 may be readily flexed or yieldably distorted when engaged with a more rigid surface. By making the entire device non-rigid, damage to the eye is avoided since the device will yield if there is an overload or undue pressure exerted. The compound curvature composed of surfaces 28 and 29 operate to more readily secure the lens 16 in position during manipulation. The plurality of ribs 21-23 inclusive provide a firm gripping indication or feel to the user and also operate to rapidly expand the bulb when the fingers release pressure on the bulb.

It is to be particularly noted that passageway 13 is of a minimum diameter in order to effect a positive jet-like stream of air into the reduced area 25 of the lens seat. This causes an immediate dispersal of air to the outermost edges of the lesser cup portion or surface 28 permitting a balanced and wider air wedge to gently bring about the total separation of the lens from the cup or lens seat.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A contact lens applicator for inserting and removing a contact lens in and from the eye of a user comprising the combination of:
   a pliable bulb-like element having an internal cavity;
   an elongated flexible shank having one end detachable connected to said bulb-like element;
   a cup-like element integrally carried on the opposite end of said shank and exposing a compound concave curvature surface establishing a lens seat for carrying said contact lens;
   said shank provided with an open-ended passageway in communication with said bulb-like element cavity and said lens seat for expelling air from said cavity when said bulb-like element is compressed;
   said cup-like element is joined to said shank by a shank portion of reduced diameter whereby the flexibility of said shank is greater than the flexibility of the remainder of said shank;
   said compound concave curvature comprises a pair of concave surfaces of different diameter coaxially disposed with respect to said shank passageway; and
   said bulb-like element includes a series of integrally formed reinforcement ribs projecting from the wall of said element into said cavity wherein said ribs strengthen said bulb-like element and bias the wall thereof to expand into its original shape.

2. The invention as defined in claim 1 wherein said one end of said shank and end of said bulb-like element receiving said shank are provided with mating and corresponding beads and depressions so as to constitute a snap-lock connection therebetween.

3. The invention as defined in claim 2 wherein said shank and said bulb-like element constitute a molded two part construction.

4. The invention as defined in claim 1 wherein said shank includes a nob on said one end and a flange in spaced apart relationship thereto as separated by a reduced diameter portion of said shank; and
   said bulb-like element includes an annular shoulder occupying the area adjacent said reduced diameter portion between said flange and said nob so as to provide an engagement therebetween.

5. The invention as defined in claim 4 wherein said nob includes a tapered outer surface converging to terminate at a flat end.

6. The invention as defined in claim 5 including a stop means for releasably holding said shank to said bulb-like element.

7. A contact lens applicator for inserting and removing a contact lens in and from the eye of a user comprising the combination of:
   a pliable bulb-like element having an internal cavity;

an elongated flexible shank having one end detachably connected to said bulb-like element;

a cup-like element integrally carried on the opposite end of said shank and exposing a compound concave curvature surface establishing a lens seat for carrying said contact lens;

said shank provided with an open-ended passageway in communication with said bulb-like element cavity and said lens seat for expelling air from said cavity when said bulb-like element is compressed;

said cup-like element includes a lens seat composed of a pair of different diametered concave and concentric curvatures coaxially disposed with respect to said passageway;

said shank having a reduced diameter portion adjacent said cup-like element for flexibly carrying said element; and said bulb-like element having a plurality of integral, internal ribs for reinforcing a wall of said bulb-like element and for forcibly biasing said wall into a non-compressed position.

* * * * *